(12) United States Patent
Cummins et al.

(10) Patent No.: US 7,192,618 B2
(45) Date of Patent: Mar. 20, 2007

(54) ANTIMICROBIAL COMPOSITION FOR PRE-HARVEST AND POST-HARVEST TREATMENT OF PLANTS AND ANIMALS

(75) Inventors: Barry W. Cummins, Ft. Pierce, FL (US); David H. Creasey, Vero Beach, FL (US)

(73) Assignee: Tasker Products IP Holdings Corp., Conroe, TX (US)

( * ) Notice: Subject to any disclaimer, the term of this patent is extended or adjusted under 35 U.S.C. 154(b) by 259 days.

(21) Appl. No.: 10/922,604

(22) Filed: Aug. 20, 2004

(65) Prior Publication Data

US 2005/0191394 A1    Sep. 1, 2005

Related U.S. Application Data

(60) Provisional application No. 60/547,991, filed on Feb. 26, 2004.

(51) Int. Cl.
*A23B 4/12* (2006.01)
*A23B 4/24* (2006.01)

(52) U.S. Cl. .................. 426/321; 426/322; 426/330.3; 426/331; 426/332; 426/333; 426/335

(58) Field of Classification Search ................ 426/321, 426/322, 330.3, 331, 332, 333, 335
See application file for complete search history.

(56) References Cited

U.S. PATENT DOCUMENTS

| | | | | |
|---|---|---|---|---|
| 5,961,843 A | * | 10/1999 | Hayakawa et al. | 210/748 |
| 5,989,595 A | * | 11/1999 | Cummins | 424/710 |
| 5,997,911 A | | 12/1999 | Brinton et al. | 424/632 |
| 6,242,011 B1 | * | 6/2001 | Cummins | 424/710 |
| 6,506,737 B1 | | 1/2003 | Hei et al. | 514/75 |
| 6,565,893 B1 | | 5/2003 | Jones et al. | 424/616 |
| 2003/0118705 A1 | | 6/2003 | Cook et al. | 426/322 |
| 2005/0155939 A1 | * | 7/2005 | Stadelmann | 210/764 |

FOREIGN PATENT DOCUMENTS

JP    02001347274 A    * 12/2001

* cited by examiner

*Primary Examiner*—Helen Pratt
(74) *Attorney, Agent, or Firm*—Sonnenschein Nath & Rosenthal LLP

(57) ABSTRACT

An antimicrobial, anti-bacterial processing aid, food additive and food ingredient is provided to inhibit cellular growth of known pathogenic, indicator and spoilage organisms, such as *salmonella, stahphylococcus, listeria, e coli,* and the like. The antimicrobial agent of the present invention is useful as a treatment for animal feed, a treatment for pre-harvest and post-harvest processing of foodstuffs, a treatment for cooked food subject to airborne contaminants and many other conditions in need of disinfectants and sanitizers. One of the primary benefits of the antimicrobial agent is that it inhibits the growth of bacteria that have become antibiotic resistant.

26 Claims, 2 Drawing Sheets

ANTIMICROBIAL COMPOSITION FOR PRE-HARVEST AND POST-HARVEST TREATMENT OF PLANTS AND ANIMALS

This invention claims the benefit of priority based on the U.S. Provisional Application Ser. No. 60/547,991 filed Feb. 26, 2004.

FIELD OF THE INVENTION

This invention relates to an antimicrobial agent and in particular to a composition of matter, a method of making and using the composition of matter for antimicrobial, anti-bacterial, pre-harvest and post harvest treatment of foodstuffs to inhibit cellular growth of known pathogenic, indicator and spoilage organisms that contaminate the human food chain.

BACKGROUND AND PRIOR ART

Protein sources in the human food chain, such as, eggs, raw meats, poultry, game birds, milk and dairy products, fish, shrimp, frog legs, and the like, carry the potential for nourishment and the potential for illness and death. Edible vegetation in the human diet, such as fruit, vegetables, and crops harvested and handled in contaminated environments can also carry the potential for illness and death. Well-known pathogens such as *salmonella, listeria* and *e-coli*, as well as indicator and spoilage organisms, including *staph* bacteria can be found prior and during the processing or harvesting of raw meats, fruit, vegetables or in partially cooked foodstuffs and animal products consumed by humans.

The globalization of business, travel and communication brings increased attention to worldwide exchanges between communities and countries, including the potential globalization of the bacterial ecosystem. Harmful bacteria were once controlled with antibiotics, such as penicillin, in the mid-1940s; but the control no longer exists as more and more antibiotic resistant bacteria appear around the globe. For example, before 1946 about 90 percent of *Staphylococcus aureus* isolates in hospitals were susceptible to penicillin, by 1952, 75 percent of isolates were penicillin-resistant. Bacterial resistance to antimicrobial agents has emerged, throughout the world, as one of the major threats both in human and veterinary medicine. Resistance to antibiotics and antimicrobial agents has emerged at an alarming rate because of a variety of factors, such as clustering and overcrowding, the use of antibiotics in animal culture and aquaculture, an increase in the number of elderly people, increased traveling, the sale of antibiotics over the counter, self-treatment with antibiotics, a lack of resources for infection control, and the inappropriate use of antibiotics.

Thus, the world population is at increased risk for acquiring antimicrobial-resistant foodborne infections. Even a small increase in the prevalence of resistance in the most significant pathogenic bacteria may lead to large increases in the potential for treatment failures and other adverse outcomes, including death.

Appropriate use of antimicrobial agents in humans and food animals is necessary to maintain the antimicrobial effectiveness and reduce the potential for the spread of resistant organisms. While therapeutic usage of antimicrobial agents in food animals is important to promote animal health and provide an affordable supply of meat, milk, and eggs, it is vital that the long-term effectiveness of antimicrobial agents used in human medicine be preserved. The present invention provides an antimicrobial processing aid and food additive for which there is no known resistance and can be used to protect public health.

In U.S. Pat. Nos. 5,989,595 and 6,242,011 B1 to Cummins, an acidic composition of matter is disclosed that is useful for destroying microorganisms that spoil food, such as fish. The composition of matter, patented by Cummins, is also useful for skin treatment of melanoma and the treatment of other bacteria, and serves as the precursor for the novel antimicrobial agent of the present invention.

U.S. Pat. No. 5,997,911 to Brinton et al. describe that a simple copper salt, hydroxycarboxylic acid and a buffering agent such as ammonium salts can be solubilized in drinking water for turkeys and swine in an antidiarrheal effective dosage.

U.S. Pat. No. 6,506,737 B1 to Hei et al. describe an antimicrobial composition for the food industry that may include sulfuric acid, sulfates and an ammonium halide salt to provide a gel-thickened compound for cleaning and sanitizing surfaces among other uses. The use of a halide ingredient limits usage for ingestion by man or animals and would be deleterious to machinery, plants and other vegetation.

U.S. Pat. No. 6,565,893 B1 to Jones et al. describe an aqueous disinfectant for swimming pools and the like, wherein copper sulfate pentahydrate, water, sulfuric acid and ammonium sulfate are combined in a "cold process" requiring that the formulation be maintained at a temperature above 40° F. to keep metallic ions in suspension.

U.S. Patent Pub. No. 2003/0118705 A1 to Cook et al. describe an ingestible disinfectant to eradicate and control pathogens on plants, animals, humans, byproducts of plants and animals and articles infected with pathogens; the disinfectant includes sulfuric acid, water and metallic ions, particularly copper, silver and gold.

Collectively, the above documents do not provide a halogen-free composition of matter that is stable under a wide range of temperatures and pH ranges, ingestible, and effective in both pre-harvest and post-harvest treatment of foodstuffs consumed by man and other animals. The composition of the present invention is safe and effective in an unlimited number of pre-harvest and post-harvest applications and is also safe for the environment.

SUMMARY OF THE INVENTION

The first objective of the present invention is to provide a composition of matter and method for its production that inhibits cellular growth of pathogenic organisms.

The second objective of the present invention is to provide a composition of matter and method for its production that inhibits cellular growth of indicator and spoilage organisms.

The third objective of the present invention is to provide a compositon of matter and method for its production, for use in scalding tank waters for dipping poultry and other animal carcasses.

The fourth objective of the present invention is to provide a composition of matter and method for its production, for use in water treatment processes in a meat production line, including, but not limited to, the spray bath, final rinse and chill water tank.

The fifth objective of the present invention is to provide a composition of matter and method for its production, for the treatment of wastewater.

The sixth objective of the present invention is to provide a compositon of matter and method for its production, for the treatment of animal feed and water.

The seventh objective of the present invention is to provide a composition of matter and method for its production, that can be used against a wide range of human, plant and animal diseases as well as minimize the growth and spread of diseases in plants and plant surfaces, either pre-harvest or post harvest.

The eighth objective of the present invention is to provide a composition of matter that is used as a surface disinfectant for hospitals, homes and other areas that require hard surface disinfectants.

The ninth objective of the present invention is to provide a composition of matter that inhibits the growth of pathogenic, indicator and spoilage bacteria that have become antibiotic resistant.

The tenth objective of the present invention is to provide a composition of matter for use in icemakers, so that ice used in post-harvest processing of foodstuff can perform an additional antimicrobial function.

Another objective of the present invention is to provide an antimicrobial aid to reduce microbial contamination in food items such as milk, poultry, eggs, red meat, meat from pigs, and seafood either pre-harvest, post-harvest, during and after processing.

Further objects and advantages of this invention will be apparent from the following detailed description of a presently preferred embodiment, which is illustrated in the accompanying tables and graphs.

DESCRIPTION OF THE PREFERRED EMBODIMENT

Figure 1:
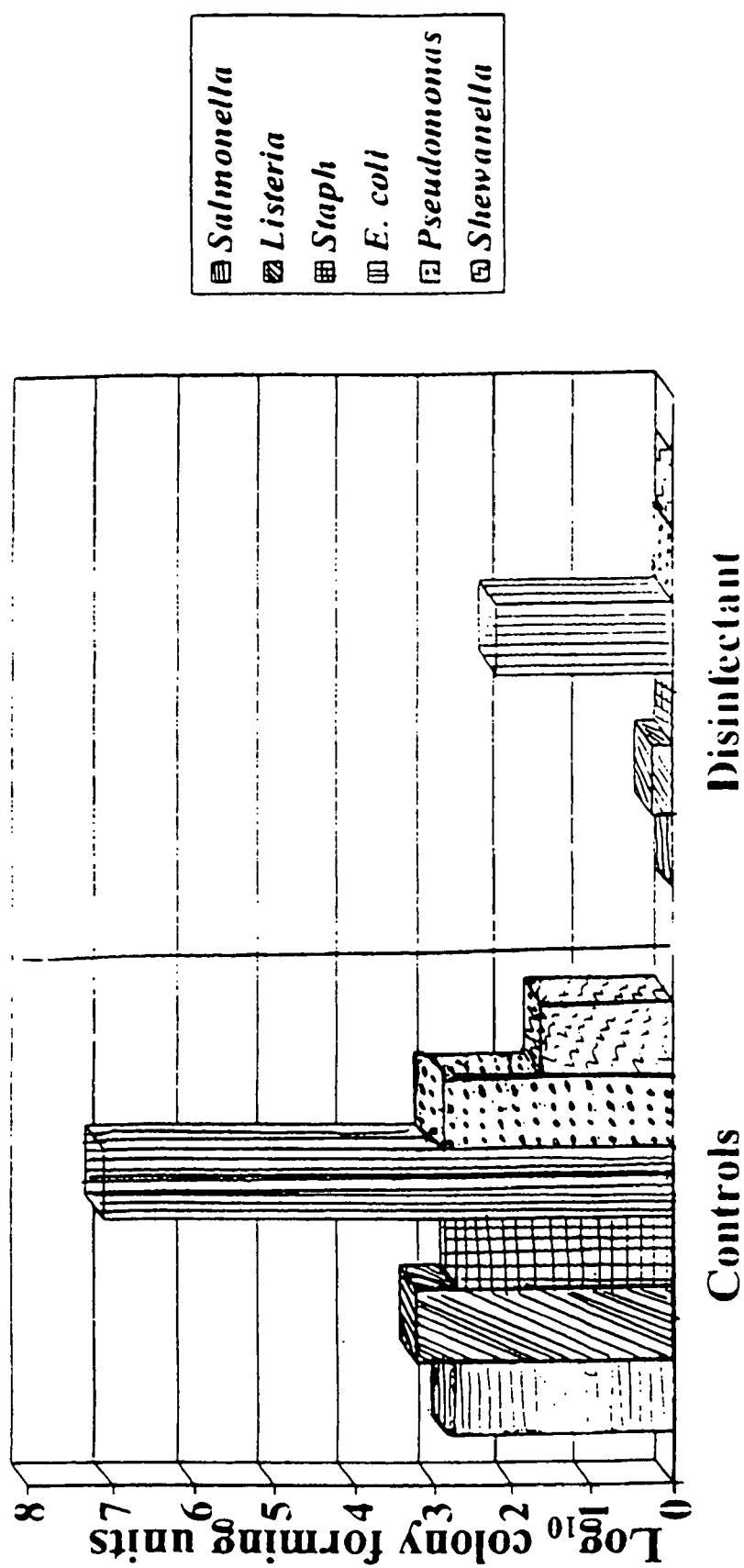
FIG. 1 is a graph showing the effect of PHB0020 on pathogenic and spoilage bacterial isolates exposed for 2 minutes.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words used herein and their applications before discussing the composition of matter and method of using and making the same:

Pre-harvest—is used herein to mean any time after birth or seed germination and before the cessation of growth and life of a plant or animal.

Post-harvest—refers to any time after the cessation of growth and life of a plant or animal and includes non-food hard surfaces involved in processing and preparing foodstuffs.

PHB0020—Copper sulfate pentahydrate and/or other forms of copper ions, and silver sulfate and/or other forms of silver ions added to pHarlo for the antimicrobial, antibacterial additive of the present invention.

PHB0028—the formulation to be used as an additive in animal feed.

PHBO128—the formulation for use as an additive to treat wastewater.

pHarlo—composition of matter claimed in U.S. Pat. Nos. 5,989,595 and 6,242,001 B1 to Cummins and incorporated herein by reference and more completely described below.

E-coli—*Escherichia coli*, indicator bacteria
Listeria—*Listeria monocytogenes*, a pathogen
Pseudomonas—*Pseudomonas fluorescens*, spoilage bacteria
Salmonella—*Salmonella typhimurium*, a pathogen
Shewanella—*Shewanella putrefaciens*, spoilage bacteria
Staph—*Staphylococcus aureus*, a pathogen The acidic composition of matter and method of making are similar to that described in U.S. Pat. Nos. 5,989,595 and 6,242,011 B1 to Cummins and are incorporated herein by reference.

First, a pressurized vessel is selected that includes a cooling jacket and no electrode attachments; however, the preferred pressurized vessel is fitted with two electrodes, a cathode and anode, to provide a direct current (DC) voltage 1 ft. above the bottom of the container. The electrodes are spaced approximately three (3) feet apart.

The processing steps of the present invention comprise combining sulfuric acid with purity in a range from approximately 94% to approximately 99.9%, in a 1 to 2 volume ratio with distilled water and ammonium sulfate in a ratio of 2.77 pounds of ammonium sulfate per gallon of distilled water to provide mixture (I). The mixture (I) is combined in the pressurized vessel having preferably two strategically placed electrodes, a cathode and anode. During the addition of ammonium sulfate, a direct current (DC) voltage is applied to the mixture. The voltage is applied in a range from approximately one (1) amp to approximately 100 amps, preferably between approximately 1 amp and approximately 5 amps. The mixture is then heated under pressure in a range of from approximately 1 pound per square inch (psi) to approximately 15 psi above atmospheric pressure. Heating of the mixture is in a range of from approximately 200° Fahrenheit (F.) to approximately 1200° F., preferably from approximately 800° F. to approximately 900° F. for approximately 30 minutes. With the application of heat and pressure as specified above, it is understood by persons skilled in the art, that a judicious selection of temperature, time and pressure is required and should be adjusted to maintain a safe chemical reaction.

After cooling the mixture, a stabilizer is added. The stabilizer is a portion of mixture (I) prior to heating in the pressure vessel. The quantity of stabilizer used is approximately 10 weight percent of the total weight of mixture (I). The resulting acidic composition is useful for destroying microorganisms, having a pH of negative 3 (−3). The inventive step of the present invention requires the addition of compounds containing metallic ions for the extensive antimicrobial properties discussed herein. The following physical and chemical properties are observed when undiluted.

pH=−3 which was determined by a non acidified hydrogen proton count with the data corrected for any electrode type errors, and was performed by EFE&H analytical services, an EPA (Environmental Protection Agency) approved laboratory stability of metallic ions in solution: from approximately 0 pH up to approximately 9 pH stability of metallic ions with temperature: from approximately 32° F. to the point of vaporization or approximately 212° F.

Various other compounds with metallic ions may be substituted for copper sulfate pentahydrate. The following metal salts are suitable substitutes:

Copper sulfate, copper glutamate, zinc oxide, zinc glutamate, magnesium glutamate, magnesium sulfate, silver sulfate, silver oxide, and combinations thereof.

Referring now to the composition of pHarlo Blue 0020, hereinafter referred to as PHB0020, it is an antimicrobial, anti-bacterial agent, which has a formulation that is generally recognized as safe (GRAS) by the US Food and Drug Administration. PHB0020 is useful in the pre-harvest and post-harvest treatment of food sources and foods, including, but not limited to, plants, fruit, vegetables, eggs, poultry, seafood, meats, and animal and pork products. The ratio of ingredients combined for processing is listed below in Table A:

TABLE A

| Ingredient | Percentage |
| --- | --- |
| Copper Sulfate Pentahydrate | 16.4 |
| Sulfuric Acid (processing aid) | 9.9 |
| Ammonium sulfate | 2.2 |
| Distilled water | 71.5 |

The ingredients form a concentrate, which is combined in small amounts of less than 0.10 milliliters (ml) with 1 gallon of water to make PHB0020.

The examples, graphs and charts below provide greater detail on the use and effectiveness of PHB0020 as an antimicrobial agent and food additive.

EXAMPLE 1

In processing plants for poultry and animal products, it is customary to use various water treatment processes, such as a scalding tank, spray bath, final rinse and chill water tank. The scalding tank is used to dip poultry prior to the removal of feathers; other animals are dipped to remove the outer coating of fur or hair. The scalding process permits cross contamination and spread of pathogens. It is important for the safety of the human food supply to provide an additive that can be used in water treatments to inhibit the growth and spread of pathogens and deleterious bacteria. The ideal additive would not evaporate at boiling point temperatures, would not be destroyed by high temperatures and would not be bound by organic material, such as blood and feces and rendered useless.

The effect of PHB0020 on pathogenic, indicator, and spoilage populations of bacteria associated with broiler chicken carcasses in a poultry scald water application is determined in one embodiment of the present invention.

First, scalder water was collected from the overflow or entrance end of a commercial poultry scalder. The water is sterilized or autoclaved to eliminate all populations of bacteria and bacterial spores to avoid interference during the study. The autoclaved scalder water is evaluated chemically and compared to raw scalder water to ensure that the organic material demand in raw and autoclaved scalder water is similar.

Next, sets of test tubes are prepared by adding 9 milliliters (ml) of sterilized scalder water to sterile polystyrene test tubes. One set is prepared as controls by adding 9 ml of sterilized scalder water to tubes. One set is prepared by adding 9 ml of sterilized scalder water and PHB0020 (the disinfectant) until the pH of 2.2 is achieved.

Each bacterium is exposed, one at a time, to the sterilized scalder water with PHB0020 sanitizer for approximately 2 minutes at approximately 130° F. (55° C.) to mimic scalding.

After the exposure period, one ml of the suspension was enumerated using the aerobic plate count method by pour plating and incubating at approximately 95° F. (35° C.) for 48 hours.

Table I below records microbial growth results in a scalder water project wherein sterilized water was heated to scalding temperatures of in a range of from approximately 120° F. (49° C.) to approximately 140° F. (60° C.), preferably to a temperature of approximately 130° F. (55° C.). Various concentrations of PHB0020 are added in a range between approximately 0.4 parts per million (ppm) to approximately 0.8 ppm, preferably at approximately 0.6 ppm and colonies of pathogens, indicator bacteria and spoilage bacteria are exposed to the treated scalder water.

TABLE I

Scalder Water Project

| Control Sample No.: | Colonies forming Bacteria Units | Log of Reduction | Growth after Exposure to Treated Scalder Water |
| --- | --- | --- | --- |
| Bacteria: *Salmonella typhimurium* | | | |
| 1 | 430 | 2.633468 | negative (no growth) |
| 2 | 880 | 2.944483 | negative |
| 3 | 970 | 2.986772 | negative |
| 4 | 450 | 2.653213 | negative |
| 5 | 620 | 2.792392 | negative |
| 6 | 700 | 2.845098 | negative |
| 7 | 1140 | 3.056905 | negative |
| 8 | 620 | 2.792392 | negative |
| 9 | 580 | 2.763428 | negative |
| Bacteria: *Staphylococcus aureus* | | | |
| 1 | 530 | 2.724276 | negative (no growth) |
| 2 | 550 | 2.740363 | one (1) colony growing |
| 3 | 580 | 2.763428 | negative |
| 4 | 500 | 2.698970 | negative |
| 5 | 540 | 2.732394 | negative |
| 6 | 420 | 2.623249 | negative |
| 7 | 530 | 2.724276 | negative |
| 8 | 480 | 2.681241 | one (1) colony growing |
| 9 | 470 | 2.672098 | negative |
| Bacteria: *Pseudomonas fluorescens* | | | |
| 1 | 540 | 2.73234 | negative |
| 2 | 880 | 2.944483 | negative |
| 3 | 790 | 2.897627 | negative |
| 4 | 620 | 2.792392 | negative |
| 5 | 1120 | 3.049218 | negative |
| 6 | 790 | 2.897627 | one (1) colony growing |
| 7 | 5200 | 3.716003 | negative |
| 8 | 1360 | 3.133539 | negative |
| 9 | 1040 | 3.017033 | negative |
| Bacteria: *Listeria monocytogenes* | | | |
| 1 | 1720 | 3.235528 | five (5) colonies growing |
| 2 | 1840 | 3.264818 | six (6) colonies growing |
| 3 | 1440 | 3.158362 | negative (no growth) |
| 4 | 1820 | 3.260071 | five (5) colonies growing |
| 5 | 1440 | 3.158362 | one (1) colony growing |
| 6 | 1880 | 3.274158 | negative |
| 7 | 1720 | 3.235528 | negative |
| 8 | 1720 | 3.235528 | negative |
| 9 | 1740 | 3.240549 | negative |
| Bacteria: *Shewanella putrefaciens* | | | |
| 1 | 50 | 1.698970 | negative (no growth) |
| 2 | 50 | 1.698970 | negative |
| 3 | 60 | 1.778151 | negative |
| 4 | 20 | 1.301030 | negative |
| 5 | 50 | 1.698970 | negative |
| 6 | 70 | 1.845098 | negative |
| 7 | 80 | 1.903090 | negative |
| 8 | 20 | 1.301030 | negative |
| 9 | 30 | 1.477121 | negative |
| Bacteria: *Escherichia coli* | | | |

TABLE I-continued

Scalder Water Project

| Control Sample No.: | Colonies forming Bacteria Units | Log of Reduction | Growth after Exposure to Treated Scalder Water |
|---|---|---|---|
| 1 | 15100000 | 7.178977 | 460 colonies growing |
| 2 | 12900000 | 7.110590 | negative (no growth) |
| 3 | 13300000 | 7.123852 | 32 colonies growing |
| 4 | 12200000 | 7.086360 | 1170 colonies growing |
| 5 | 13400000 | 7.127105 | 4700 colonies growing |
| 6 | 12200000 | 7.086360 | 57 colonies growing |
| 7 | 14200000 | 7.152288 | 900 colonies growing |
| 8 | 13600000 | 7.133539 | 410 colonies growing |
| 9 | 7600000 | 6.880814 | 37 colonies growing |

Referring now to FIG. 1, the graph shows the effect of PHB0020 on pathogenic and spoilage bacteria identified in the table above. The graph is divided in two sections, on the left is the control showing the logarithm of colony forming units for each bacterium and on the right is the graph of colony forming units after each bacterium is exposed for 2 minutes to scalder water treated with PHB0020. The graph shows that *Listeria*, a gram-positive bacterium, is hard to kill and *E coli*, a very prolific bacterium, has the highest reduction after a 2 minute exposure.

Figure 2:
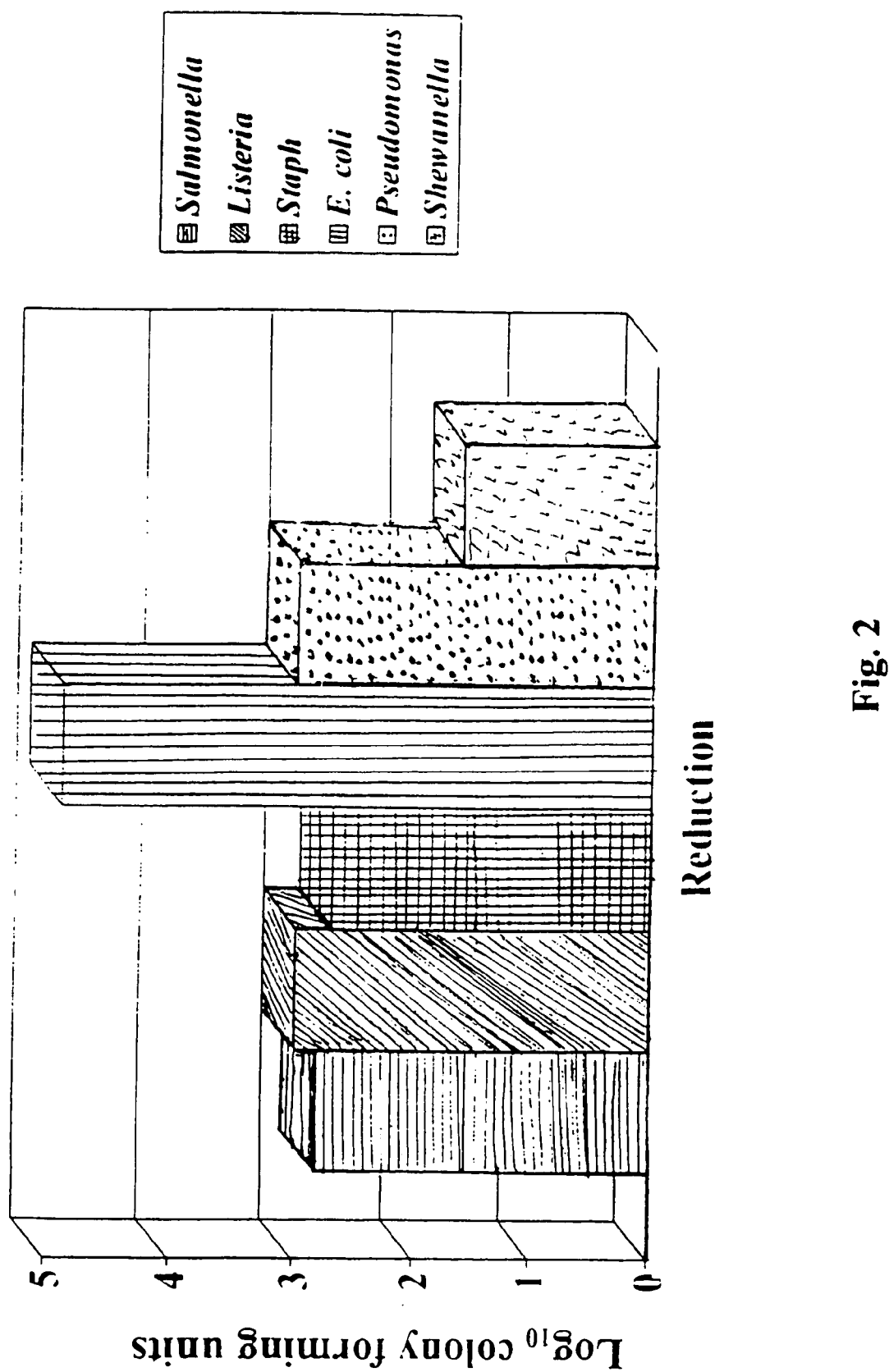
FIG. 2 is a graph showing the logarithm of reductions in bacterial colony levels.

In FIG. 2, the graph shows the logarithm of the reduction of bacterial levels for each bacterium. In most cases the log of colony forming units is less than three, with the most prolific bacterium, *E coli* having a log of less than five.

Thus, PHB0020 functions as an antimicrobial agent, disinfectant, or sanitizer and is extremely effective for eliminating populations of pathogenic, indicator and spoilage bacteria in commercial scalder water under industrial scalding conditions. PHB0020 is an effective means for controlling bacteria in scalder water and may be used for controlling cross-contamination during scalding. Disinfection of poultry scalder water is crucial because it is the first area within the plant in which birds are immersed in a common bath and bacteria may be transferred from bird to bird.

The efficacy of PHB0020 as an antimicrobial agent is suitable for many other uses and in the quantitative ranges identified below in Table J:

TABLE J

Use Levels in Milligrams per Liter (mg/l):

| | Range | Target |
|---|---|---|
| Application for PHB0020: PRE-HARVEST | | |
| Hatcheries | 1.0 to 2.0 mg/l | 1.3 mg/l |
| Egg- wash | 0.8 to 1.5 mg/l | 1.0 mg/l |
| Drinking water for livestock | 0.8 to 2.0 mg/l | 1.2 mg/l |
| Animal feed | 0.6 to 2.0 mg/l | 1.0 mg/l |
| Seafood water supply | 0.4 to 1.5 mg/l | 0.8 mg/l (species dependent) |
| Animal foot disinfectant | Approximately 1 mg/l to approximately 50 mg/l | Approximately 20 mg/l |
| POST-HARVEST Poultry: (chicken, turkey, game birds, ostrich, duck, geese, pheasants) | | |
| 1. Scalder | 0.4–0.8 to 3 mg/l | Water chemistry dependent |
| 2. Chill Tank | 0.6–1.0 mg/l | 0.8 mg/l |
| 3. Final Rinse | 0.4–0.8 mg/l | 0.6 mg/l |
| Red Meat | 0.8–1.2 mg/l | 1.0 mg/l |
| Seafood (fish, shell fish, frogs, octopus, squid) | 0.4–1.0 mg/l | 0.8 mg/l |
| Wastewater | 0.6 to 1.0 mg/l | 0.8 mg/l |
| Airborne contaminants on cooked food | 0.4 to 1.0 mg/l | 0.8 mg/l |
| Preservative coating | 0.4 to 0.8 mg/l | 0.6 mg/l |
| Ingredient in Ice Products | 0.6 to 1.0 mg/l | 0.8 mg/l |

The table above identifies some of the applications for the present invention; it is an indication of the enormous commercial potential for the novel antimicrobial composition that can be used to protect public health.

Pre-harvest and non-food uses for the composition of the present invention are discussed in further detail. The composition can be produced in several forms when diluted with distilled water, such as, an aerosol, mist, vapor or fog to produce micron sized particles that remain in suspension in the air for a period of time and act on airborne pathogens that come in contact with the composition. The composition of the present invention can remove ammonia odors from hatcheries, improve the quality of animal water supply and it can be used in solutions for washing, coating and otherwise disinfecting food products prior to harvesting, such as in hatcheries, dairies and in egg washes. Another use can be for the oral care and as a foot wash or disinfectant for dairy cattle. As would be expected, many non-food uses of the composition of the present invention can include, effective control of microbial or pathogenic populations, as found on food preparation equipment, utensils, counter tops, transport belts, boot and hand-wash-dip pans, storage facilities, air circulation systems, coolers, blanchers, walls, floors and the like.

Specific post-harvest treatment of plants and animals include, but are not limited to, aqueous treatment of plants, fruits, vegetables, animal by-products, fish and shellfish. The treatment includes washing, soaking and cleaning the food product and the composition of the present invention is effective in the scalder tank, rinse and spray streams and chiller. The end result is a safer, healthier food supply for man and other animals.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A product useful in pre-harvest and post-harvest treatment of foodstuffs to inhibit cellular growth of known pathogenic, indicator and spoilage bacteria, made by the process of: (a) combining sulfuric acid of approximately 94% purity to approximately 99.9% purity in a 1 to 2 volume ratio with distilled water and ammonium sulfate in a ratio of 2.77 pounds of ammonium sulfate per gallon of distilled water to provide mixture (I); (b) combining the mixture (I) in a pressurized vessel at a pressure that is above atmospheric pressure and heating the mixture at a temperature in a range between approximately 200 degrees Fahrenheit and approximately 1200 degrees Fahrenheit, for at least 30 minutes; (c) cooling the mixture; (d) adding a stabilizer which is a portion of mixture (I) and comprises approximately 10 weight percent of the total weight of mixture (I), thereby forming mixture (II); and (e) adding a compound containing metallic ions to mixture (II) to form mixture (III).

2. The product made by the process of claim 1, wherein the metallic ions are selected from the group consisting of copper ions, silver ions, zinc ions, magnesium ions and mixtures thereof.

3. The product made by the process of claim 1, wherein the compound containing metallic ions is selected from at least one of: copper sulfate, copper sulfate pentahydrate, copper glutamate, zinc oxide, zinc glutamate, magnesium glutamate, magnesium sulfate, silver oxide and silver sulfate.

4. The product made by the process of claim 3, wherein the compound containing metallic ions is mixed with distilled water to form a solution.

5. The product made by the process of claim 4, wherein the ratio of the distilled water solution of the compound containing metallic ions to the total weight of mixture (III) is in a range between approximately 2% to approximately 75% by weight.

6. The product made by the process of claim 1, further comprising applying direct current (DC) voltage to mixture I during the addition of ammonium sulfate.

7. The product made by the process of claim 6, wherein the DC voltage is in a range from approximately one amp to approximately 100 amps.

8. The product made by the process of claim 6, wherein the DC voltage is in a range from approximately one amp to approximately 5 amps.

9. The product of claim 1, that inhibits cellular growth of pathogenic bacteria selected from the group consisting of: *Salmonella typhimurium, Listeria monocytogenes* and *Staphylococcus aureus*.

10. The product made by the process of claim 1, that inhibits the growth of indicator bacterium *Escherichia coli*.

11. The product made by the process of claim 1, that inhibits the growth of spoilage bacteria selected from at least one of: *Pseudomonas fluorescens* and *Shewannela putrefaciens*.

12. The product made by the process of claim 1 that can be used as an additive in scalder tank water for dipping poultry in a processing production line.

13. The product made by the process of claim 1 that can be used as an additive in a water treatment process handling raw meats, the water treatment process is selected from one of: scalding, spray bath, final rinse and chill water.

14. The product made by the process of claim 1 that can be used as an additive for treatment of wastewater.

15. The product made by the process of claim 1 that can be used as a washing solution for at least one of: eggs, fruits and vegetables.

16. The product made by the process of claim 1 that can be used as an additive for animal feed.

17. The product made by the process of claim 1 that can be used as an additive for poultry feed.

18. The product made by the process of claim 1 that can be used as an additive for ice products.

19. The product made by the process of claim 1 that can be used as an antimicrobial aid to reduce microbial contamination of comestibles selected from at least one of: poultry, red meat, pork, venison, seafood, eggs, milk and dairy products.

20. The product made by the process of claim 1 that can be used to wash and disinfect the feet of dairy cattle.

21. A method of making an antimicrobial mixture for pre-harvest and post-harvest treatment of foodstuffs and non-foodstuffs, comprising the steps of: (a) adding sulfuric acid of approximately 94 percent purity to approximately 99.9 percent purity to a first container; (b) heating distilled water in a ratio of twice the volume of the sulfuric acid in a separate container to at least 140° F; (c) mixing ammonium sulfate in the heated water in a ratio of 2.77 pounds per gallon of water to form mixture (I); (d) simultaneously combining the mixture of sulfuric acid, heated distilled water, and ammonium sulfate (mixture I) into a separate pressurized vessel by injection; (e) heating the pressurized mixture to a temperature in a range between approximately 200 F. and approximately 120° F. for approximately 30 minutes to form mixture (II); (f) cooling mixture (II) and adding a stabilizer portion of mixture (I) to the cooled mixture, wherein the stabilizer comprises approximately 10 weight percent of the total weight of mixture (II); (g) adding a compound containing metallic ions to form a stable suspension (mixture III); (h) diluting the stable suspension of metallic ions to form an effective antimicrobial composition; and (i) applying the antimicrobial composition to foodstuffs and non-foodstuffs.

22. The method of claim 21, wherein the metallic ions are selected from the group consisting of copper ions, silver ions, zinc ions, magnesium ions and mixtures thereof.

23. The method of claim 21, wherein the compound containing metallic ions is selected from at least one of: copper sulfate, copper sulfate pentahydrate, copper glutamate, zinc oxide, zinc glutamate, magnesium glutamate, magnesium sulfate, silver oxide and silver sulfate.

24. A stable antimicrobial mixture comprising metallic salts, sulfuric acid, ammonium sulfate and distilled water wherein the metallic ions remain in suspension at pH ranges between approximately 0 pH to approximately 9 pH and at temperatures between approximately 32° F. and approximately 212° F.

25. The antimicrobial mixture of claim 24, wherein the metallic salts are selected from at least one of the following compounds: copper sulfate, copper sulfate pentahydrate, copper glutamate, zinc oxide, zinc glutamate, magnesium glutamate, magnesium sulfate, silver oxide, silver sulfate and mixtures thereof.

26. The antimicrobial mixture of claim 24, wherein the metallic salts comprise ions selected from the group consisting of copper ions, silver ions, zinc ions, magnesium ions and mixtures thereof.

* * * * *